United States Patent
Gysling

(10) Patent No.: US 8,428,892 B2
(45) Date of Patent: Apr. 23, 2013

(54) VISCOUS FLUID FLOW MEASUREMENT USING A DIFFERENTIAL PRESSURE MEASUREMENT AND A SONAR MEASURED VELOCITY

(75) Inventor: Daniel L. Gysling, Glastonbury, CT (US)

(73) Assignee: Expro Meters, Inc., Wallingford, CT (US)

( * ) Notice: Subject to any disclaimer, the term of this patent is extended or adjusted under 35 U.S.C. 154(b) by 471 days.

(21) Appl. No.: 12/575,908

(22) Filed: Oct. 8, 2009

(65) Prior Publication Data

US 2010/0094569 A1 Apr. 15, 2010

Related U.S. Application Data

(60) Provisional application No. 61/103,754, filed on Oct. 8, 2008.

(51) Int. Cl.
*G01F 1/00* (2006.01)
*G01F 7/00* (2006.01)
*G01F 1/12* (2006.01)
*G01F 1/50* (2006.01)
*G01F 25/00* (2006.01)
*G01F 27/00* (2006.01)

(52) U.S. Cl.
USPC .................................. 702/47; 702/100

(58) Field of Classification Search .............. 702/47, 702/100
See application file for complete search history.

(56) References Cited

U.S. PATENT DOCUMENTS

| 6,151,557 | A | 11/2000 | Broden et al. |
| 6,352,001 | B1 | 3/2002 | Wickert et al. |
| 6,422,092 | B1 * | 7/2002 | Morrison et al. .......... 73/861.04 |
| 7,000,463 | B1 * | 2/2006 | Shajii et al. .................. 73/202.5 |
| 7,328,113 | B2 | 2/2008 | Rothman et al. |
| 7,389,187 | B2 | 6/2008 | Kersey et al. |
| 7,418,877 | B2 | 9/2008 | Gysling |
| 7,636,640 | B2 * | 12/2009 | Wang et al. ..................... 702/45 |
| 2006/0053902 | A1 * | 3/2006 | Good et al. ................ 73/861.52 |
| 2007/0067116 | A1 * | 3/2007 | Rothman et al. ................ 702/55 |
| 2007/0244654 | A1 * | 10/2007 | Ito et al. .......................... 702/45 |
| 2010/0191481 | A1 * | 7/2010 | Steven ............................. 702/47 |

FOREIGN PATENT DOCUMENTS

WO 2008025935 3/2008

* cited by examiner

*Primary Examiner* — Michael Nghiem
(74) *Attorney, Agent, or Firm* — O'Shea Getz P.C.

(57) ABSTRACT

A method and apparatus for determining a parameter of fluid flow within a piping system is provided. The method includes the steps of: determining a measured velocity of the fluid flow using a fluid flow meter; determining a measured difference in pressure value within the fluid flow using a differential pressure meter; selecting an estimated Reynolds number of the fluid flow; determining a calculated difference in pressure value using a model which relates the calculated difference in pressure value to the measured velocity and the estimated Reynolds number of the fluid flow; determining a degree of inaccuracy of the estimated Reynolds number using the measured difference in pressure and the calculated difference in pressure; and iteratively adjusting the estimated Reynolds number, determining the calculated difference in pressure, and determining the degree of inaccuracy using the adjusted Reynolds number, until the degree of inaccuracy is within an acceptable range.

12 Claims, 4 Drawing Sheets

VISCOUS FLUID FLOW MEASUREMENT USING A DIFFERENTIAL PRESSURE MEASUREMENT AND A SONAR MEASURED VELOCITY

CROSS-REFERENCE TO RELATED PATENT APPLICATIONS

This application claims the benefit of U.S. Provisional Patent Application No. 61/103,754 filed Oct. 8, 2008.

BACKGROUND OF THE INVENTION

1. Technical Field

The present invention relates to apparatus and methods for fluid flow measurement in general, and to apparatus and methods for fluid flow measurement operable to determine a Reynolds number for the fluid flow in particular.

2. Background Information

SONAR type fluid flow meters operable to measure flow parameters traveling through a pipe can be calibrated as a function of the Reynolds number of the fluid flow. The Reynolds number (Re) may be described as a dimensionless number that gives a measure of the ratio of inertial forces ($\rho L^2 V^2$) to viscous forces ($\mu LV$). The Reynolds number of a fluid flow may be mathematically represented as follows:

$$Re = \frac{\rho V L}{\mu} \quad \text{(Eqn. 1)}$$

where "$\rho$" is the fluid density, "$V$" is the velocity of the fluid, "$L$" is the length scale, and "$\mu$" is the coefficient of viscosity. Typically, SONAR fluid flow meters are operated using an estimated flow viscosity to calculate an estimated Reynolds number for the fluid flow to apply the Reynolds number based calibration. This approach works reasonably well as long as the flow meter is operating at a sufficiently high Reynolds number such that the actual flow measurement is not strongly dependent on the actual Reynolds number. However, for low Reynolds number flows or flows with variable fluid viscosity, errors resulting from differences between the estimated Reynolds number and the actual Reynolds number can lead to significant error in the determined fluid flow rate.

In oil processing applications, the viscosity of oil is often not well known and can change significantly with temperature. Consequently, the Reynolds number of the fluid flow (which is related to the viscosity of the fluid flow) changes significantly as well. The calibration curve shown in FIG. 1 illustrates the relationship between Reynolds number (Re) and the ratio of a measured velocity ($V_{measured}$; i.e., an uncompensated velocity reported by a flow velocity meter) to an actual velocity ($V_{actual}$; i.e., the volumetrically averaged flow velocity) for a given fluid flow as determined by comparing the raw meter output to a calibrated reference flow velocity. The curve illustrated within FIG. 1 can be described mathematically as:

$$\frac{V_{measured}}{V_{actual}} = 1 + c_0 + \frac{c_1}{Re^{c_2}} \quad \text{(Eqn. 2)}$$

Examples of empirically determined values that can be assigned to the variables in Equation 2 include $c_0=0.03$, $c_1=23.1$, and $c_2=0.61$; these values are examples of values that can be used to define the curve in an oil/gas application. Specific values for the variables will depend upon the application at hand. It can be seen from this exemplary calibration curve that if a high Reynolds number approximation (e.g., $Re>10^6$) is appropriate for the application at hand, relatively large differences in Reynolds number will yield relatively small changes in the ratio of measured velocity to actual velocity. On the other hand, if a low Reynolds number approximation (e.g., $Re<10^4$) is appropriate for the application at hand, relatively small differences in Reynolds number will yield relatively large changes in the ratio of measured velocity to actual velocity. In short, the potential for error in determining a flow parameter (e.g., flow velocity) is greatly increased for a fluid flow meter when sensing low viscosity fluid flows, unless an accurate Reynolds number is used.

SUMMARY OF THE INVENTION

According to an aspect of the present invention, a method for determining a parameter of fluid flow within a piping system is provided. The method includes the steps of: a) determining a measured velocity of the fluid flow within the piping system using a fluid flow meter; b) determining a measured difference in pressure value within the fluid flow using a differential pressure meter; c) selecting an estimated Reynolds number of the fluid flow; d) determining a calculated difference in pressure value using a model which relates the calculated difference in pressure value to the measured velocity and the estimated Reynolds number of the fluid flow; e) determining a degree of inaccuracy of the estimated Reynolds number using the measured difference in pressure and the calculated difference in pressure; and f) iteratively adjusting the estimated Reynolds number, determining the calculated difference in pressure, and determining the degree of inaccuracy using the adjusted Reynolds number, until the degree of inaccuracy is within an acceptable range.

According to another aspect of the present invention, an apparatus for determining a parameter of fluid flow within a piping system is provided. The apparatus includes a fluid flow meter, a differential pressure meter, and a processor. The fluid flow meter is operable to determine the velocity of the fluid flow within the piping system. The differential pressure meter is operable to determine a measured difference in pressure within the fluid flow within the piping system. The processor is adapted to receive input including an estimated Reynolds number of the fluid flow. The processor is further adapted to determine a calculated difference in pressure value using a model which relates the calculated difference in pressure value to a measured fluid flow velocity and the estimated Reynolds number of the fluid flow. The processor is further adapted to determine a degree of inaccuracy of the estimated Reynolds number using the measured difference in pressure and the calculated difference in pressure, and to iteratively adjust the estimated Reynolds number, determine the calculated difference in pressure steps, and determine the degree of inaccuracy until the degree of inaccuracy is within an acceptable range.

The present apparatus and advantages associated therewith will become more readily apparent in view of the detailed description provided below, including the accompanying drawings.

DETAILED DESCRIPTION

Figure 2:
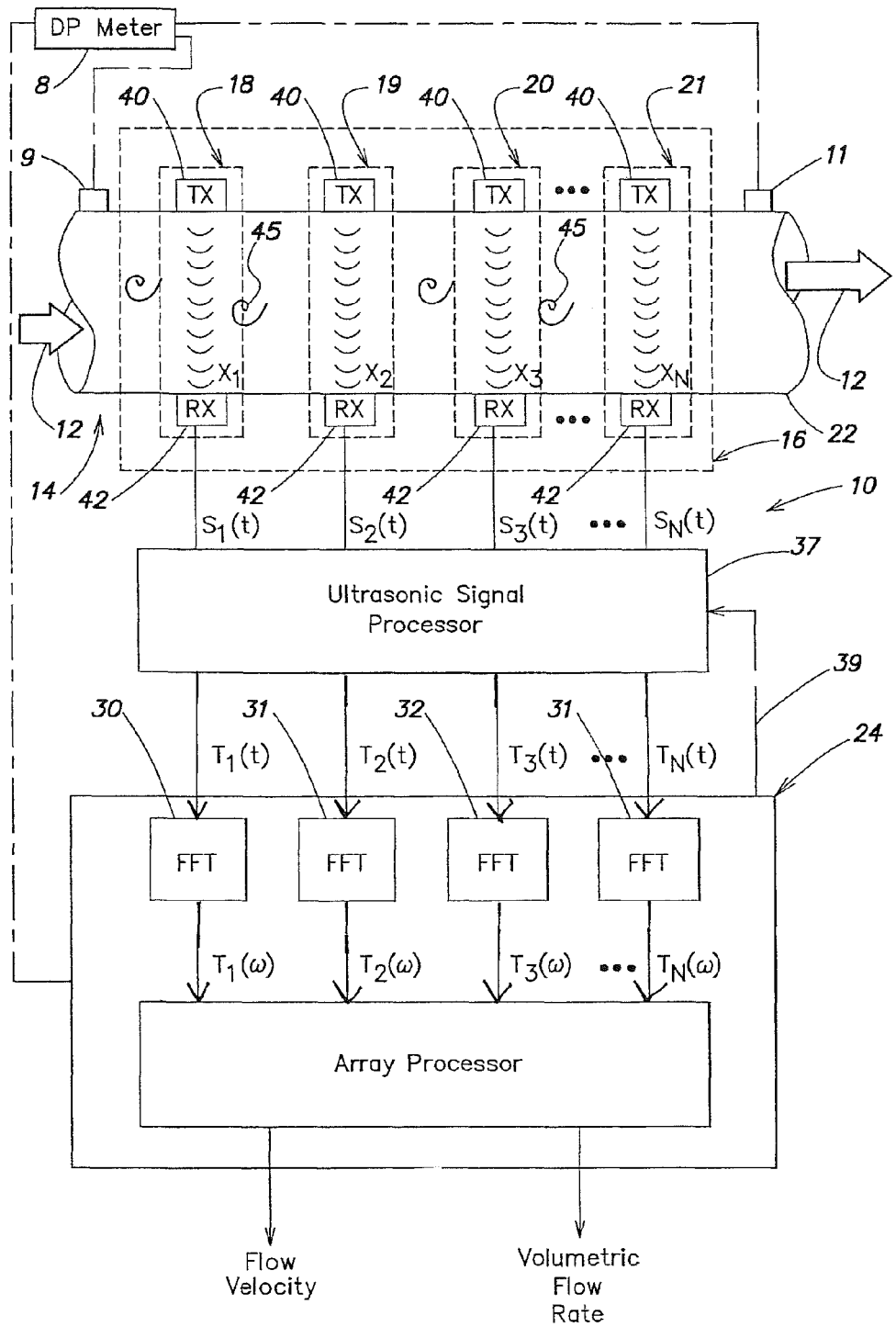
FIG. 2 is a block diagram of a fluid flow meter having an array of ultrasonic sensor units disposed axially along a pipe.

Referring to FIG. 2, the present invention provides both an apparatus and method for accurately determining flow parameters of fluid flows within a conduit (e.g., a pipe), and in particular high viscosity fluid flows, or fluid flows having a viscosity that varies over time, using a differential pressure meter 8 ("DP meter") and a fluid flow meter 10. To simplify the description below, the conduit is referred to as a pipe. The present invention is not limited to sensing fluid flow within a pipe, however.

The DP meter 8 may include any type of meter that can determine a differential pressure (ΔP) in the fluid flow. For example, the DP meter 8 may include a first pressure transducer 9 operable to measure the pressure of the fluid flow at a first position along the axial length of the pipe 14 and a second pressure transducer 11 operable to measure the pressure at a second position axial position, where a fixed geometry of pipe 14 having a axial length "L" is disposed between the two positions.

The fluid flow meter 10 is operable to determine the velocity of the fluid flow within the pipe ("$V_{measured}$"). An example of an acceptable fluid flow meter is the SONAR fluid flow meter described in U.S. Pat. No. 7,389,187 entitled "Apparatus and Method for Using an Array of Ultrasonic Sensors for Determining the Velocity of a Fluid Within a Pipe", which patent is hereby incorporated by reference in its entirety. To facilitate the description of the present invention, the fluid flow meter example described in the '187 patent will be at least partially described herein. The present invention is not limited to using this fluid flow meter 10, or any other particular fluid flow meter.

The fluid flow meter 10 includes a sensing device 16 comprising an array of ultrasonic sensor units 18-21. Each sensor unit comprises a pair of ultrasonic sensors 40,42, one of which functions as a transmitter (Tx) 40 and the other as a receiver (Rx) 42. The sensor units 18-21 are spaced axially along the outer surface 22 of a pipe 14 having a process flow 12 propagating therein. The sensors 40,42 within each pair are diametrically disposed on the pipe 14 at predetermined locations along the pipe to provide a through transmission configuration, such that the sensors transmit and receive an ultrasonic signal that propagates through the fluid substantially orthogonal to the direction of the flow of the fluid within the pipe. The flow meter 10 is not limited to this particular transmitter/receiver configuration.

As shown in FIG. 2, each pair of ultrasonic sensors 40,42 measures a transit time (i.e., time of flight (TOF), or phase modulation) of an ultrasonic signal propagating through the fluid 12 from the transmitting sensor 40 to the receiving sensor 42. The transit time measurement or variation is indicative of one or more coherent properties that convect with the flow within the pipe (e.g., vortical disturbances, inhomogenieties within the flow, temperature variations, bubbles, particles, pressure disturbances), which are indicative of the velocity of the process flow 12. The ultrasonic sensors may operate at a variety of different frequencies. There is, however, likely an optimum sensor frequency range associated with the particular application at hand Examples of frequencies used for a flow meter embodying the present invention used in oil and gas applications are 1 MHz and 5 MHz. The ultrasonic sensors may also provide a pulsed, chirped or continuous signal through the fluid flow 12. An example of the sensors 40,42 that may be used are Model no. 113-241-591, manufactured by Krautkramer.

An ultrasonic signal processor 37 fires the sensors 40 in response to a firing signal 39 from the processor 24 and receives the ultrasonic output signals $S_1(t)$-$S_N(t)$ from the sensors 42. The signal processor 37 processes the data from each of the sensor units 18-21 to provide an analog or digital output signal $T_1(t)$-$T_N(t)$ indicative of the time of flight or transit time of the ultrasonic signal through the fluid. The signal processor 37 may also provide an output signal indicative of the amplitude (or attenuation) of the ultrasonic signals. One such signal processor is model no. USPC 2100 manufactured by Krautkramer Ultrasonic Systems.

The output signals ($T_1(t)$-$T_N(t)$) of the ultrasonic signal processor 37 are provided to the processor 24, which processes the transit time measurement data to determine one or both of the flow velocity and the volumetric flow rate. As indicated above, the transit time is defined as the time it takes for an ultrasonic signal to propagate from the transmitting sensor 40 to the respective receiving sensor 42 through the pipe wall and the fluid 12. The effect of the vortical disturbances (and/or other inhomogenities within the fluid) on the transit time of the ultrasonic signal is to delay or speed up the transit time. Therefore, each sensing unit 18-21 provides a respective output signal $T_1(t)$-$T_N(t)$ indicative of the variations in the transit time of the ultrasonic signals propagating orthogonal to the direction of the fluid 12. The present invention does not require the processor 24 be adapted to any particular signal processing technique, and therefore known techniques such as k-ω plot, cross-correlation, etc., can be used and will not be further described herein.

Figure 3:
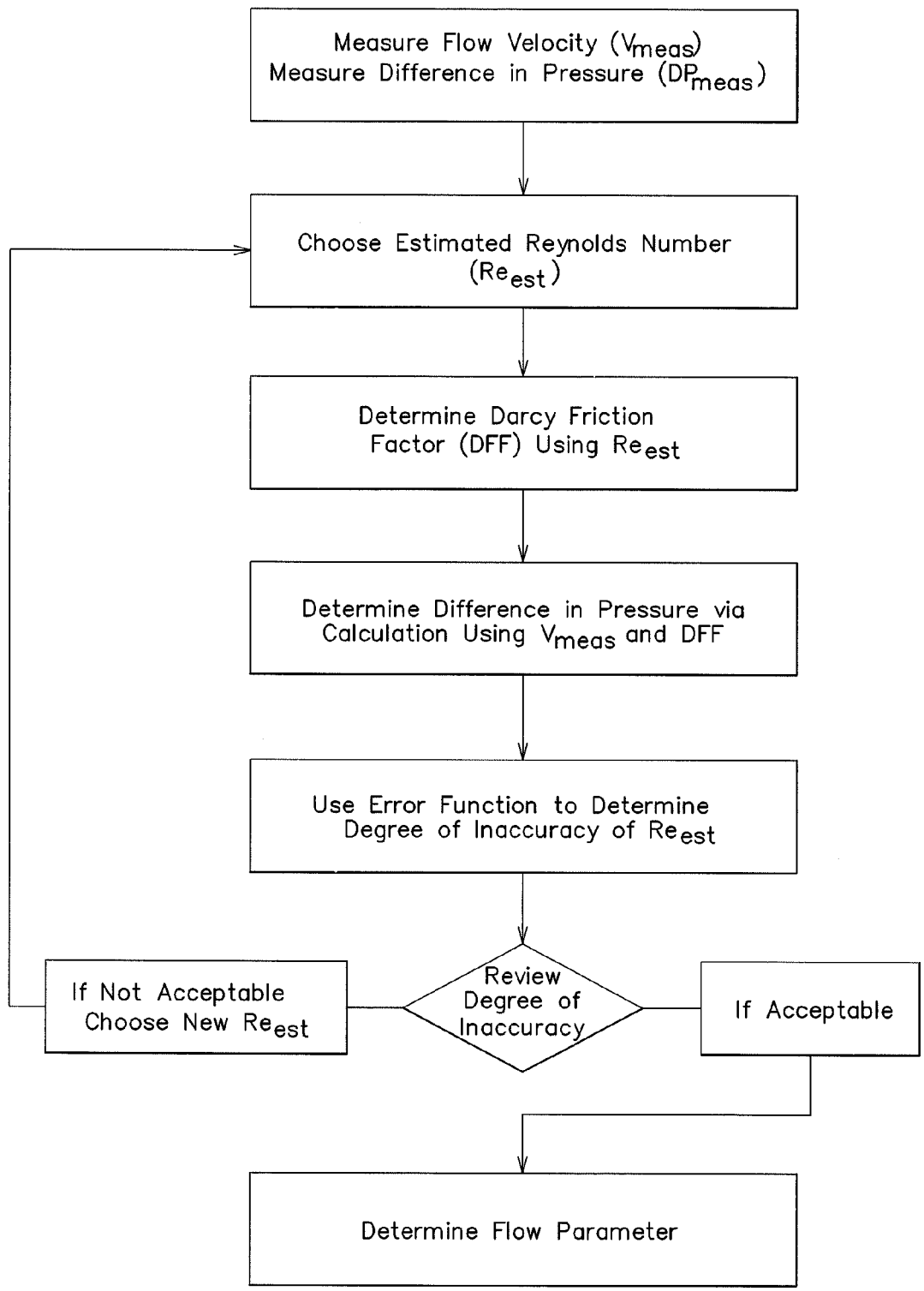
FIG. 3 is a block diagram illustrating steps within the present method and those to which the processor of the present apparatus is adapted.

Now referring to FIG. 3, under the present invention, the processor 24, alone or in combination with another processor (collectively referred to hereinafter as processor 24), is adapted to determine an initial flow velocity value ($V_{measured}$) and difference in pressure within the fluid flow ($DP_{measured}$), using the fluid flow meter and the DP meter, respectively. The processor is adapted to receive an estimated Reynolds number ($Re_{est}$) that is selected by the end user to be appropriate for the flow application/piping system at hand.

Figure 4:
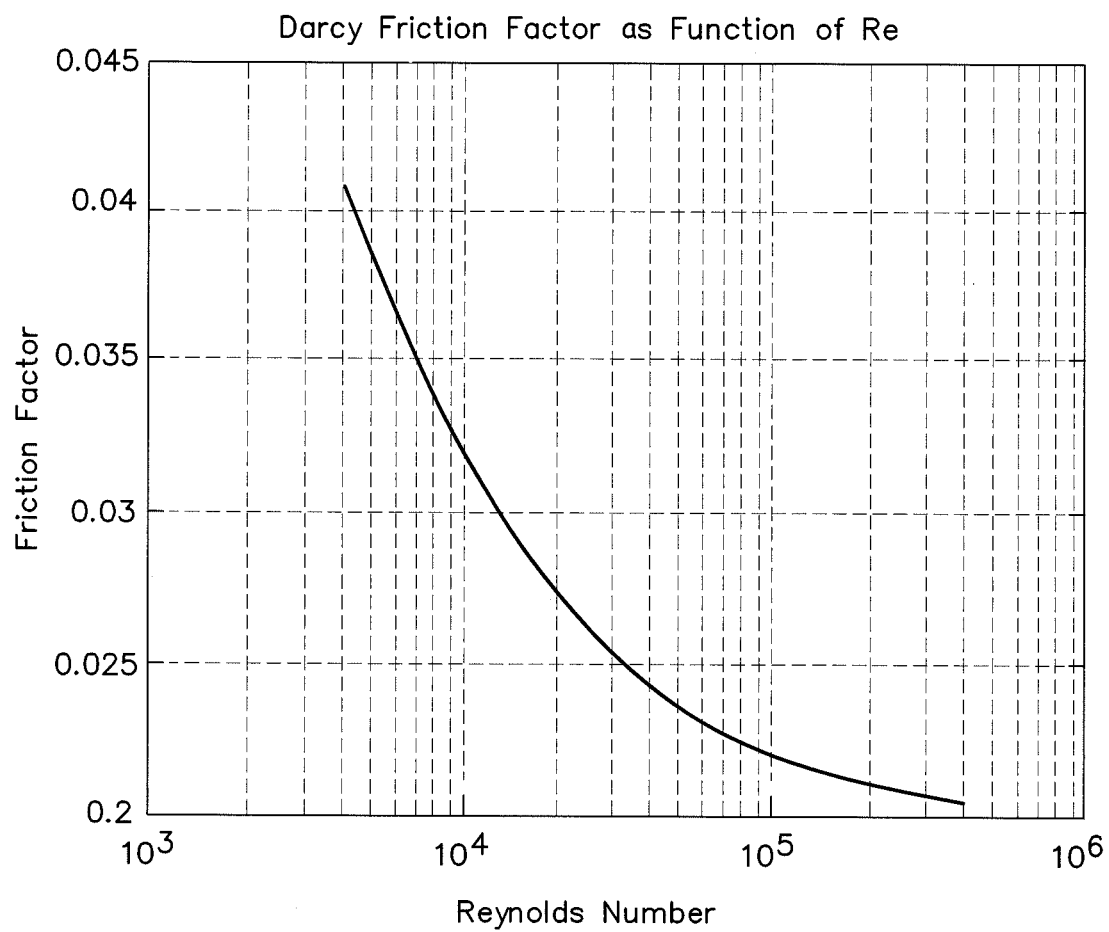
FIG. 4 is a diagrammatic graph illustrating the relationship between the Darcy Friction Factor and Reynolds number of a fluid flow.

Once the fluid flow velocity within the piping system and difference in pressure within the fluid flow are determined, the processor is adapted to use those values and the estimated Reynolds number to determine the Darcy Friction Factor (f) for the piping system. FIG. 4 diagrammatically illustrates the Darcy Friction Factor as a function of the Reynolds number for a fluid flow. The Darcy Friction Factor relates the pressure loss due to friction along a given length of pipe to the average velocity of the pipe. The Darcy Friction Factor can also be described as a function of pipe parameters and the Reynolds number of the fluid flow using, for example, the Haaland Equation:

$$\frac{1}{\sqrt{f}} = -1.8\log\left[\left(\frac{\varepsilon/D}{3.7}\right)^{1.11} + \frac{6.9}{Re}\right] \quad \text{Eqn. 3}$$

where "ε" is the roughness height on the pipe wall, and "D" is the inner diameter of the pipe. The Haaland Equation is an example of an expression relating the friction factor of the piping system, the relative wall roughness of the piping system (ε/D), and the Reynolds number of the fluid flow. The present invention is not limited to this expression and alternative expressions can be used to relate the friction factor of the pipe to the Reynolds number of the fluid flow (e.g., Colebrook Equation, etc.).

The processor is further adapted to calculate a difference in pressure ($DP_{calculated}$) using the measured fluid flow velocity within the piping system, and the determined Darcy Friction Factor (f). An example of an expression that can be used to determine the calculated difference in pressure ($DP_{calculated}$) is the Darcy-Weisbach Equation:

$$\Delta P = f\left(\frac{L}{D}\right)\left(\frac{1}{2}\rho V^2\right) \qquad \text{Eqn. 4}$$

where "V" is the volumetrically averaged flow velocity, "L" is the length of pipe, "D" is the diameter of the pipe, "ρ" is the fluid density, and "ΔP" can be $DP_{calculated}$. Many empirical models exist where the friction factor (f) is a function of the Reynolds number of the flow, and the present invention is therefore not limited to using the Darcy-Weisbach Equation.

Once the calculated difference in pressure ($DP_{calculated}$) is determined, the processor is adapted to use the calculated difference in pressure ($DP_{calculated}$) and the difference in pressure measured within the fluid flow ($DP_{measured}$) to determine a degree of inaccuracy of the estimated Reynolds number ($Re_{est}$). Any difference between the calculated difference in pressure ($DP_{calculated}$) and the measured difference in pressure ($DP_{measured}$) can then be evaluated to determine whether it is within an acceptable predetermined range. The exact values of the error range will depend upon the application at hand; e.g., the type of fluid flow, viscosity and velocity of the fluid, etc. The evaluation may utilize an error function that indicates the degree of inaccuracy of the estimated Reynolds number. The error function, which can be referred to as "$Chi^2$", is not limited to any particular expression. An example of an acceptable error function is as follows:

$$Chi^2 = \left[\frac{(DP_{measured} - DP_{calculated})}{DP_{measured}}\right] \qquad \text{Eqn. 5}$$

Figure 1:
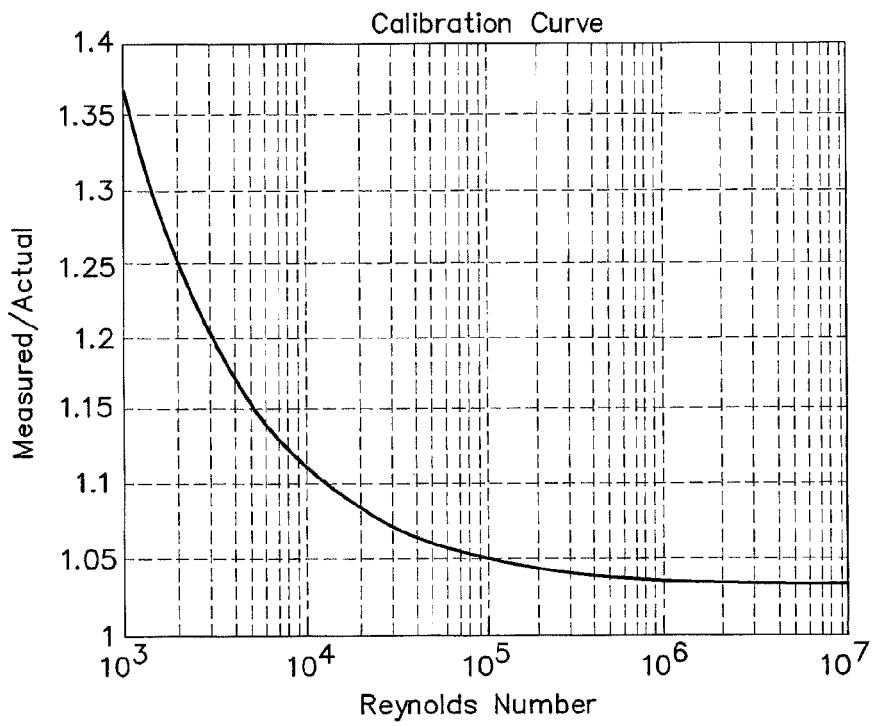
FIG. 1 is a diagrammatic graph illustrating the relationship between the Reynolds number of a fluid flow, and the ratio of measured velocity of the fluid flow to actual velocity of the volumetrically averaged velocity of the fluid flow.
Figure 5:
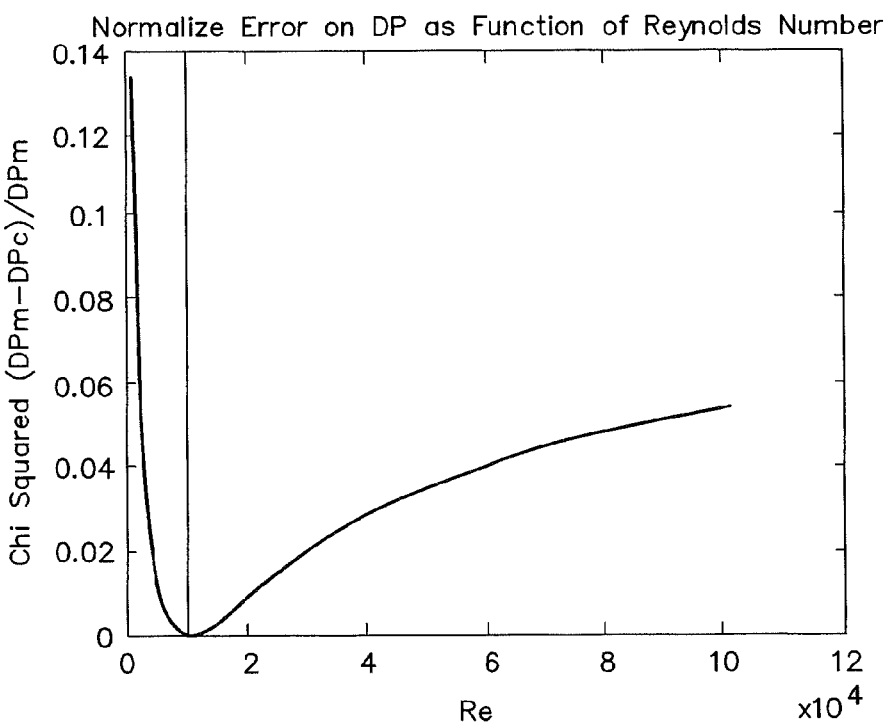
FIG. 5 is a diagrammatic illustration of the relationship between an error function embodiment and Reynolds number of a fluid flow.

A Reynolds number for the fluid flow within the piping system with an acceptable accuracy is determined under the present invention by iteratively performing the process described above; i.e., updating the estimated Reynolds number each time and using it to determine the Darcy Friction Factor and the calculated difference in pressure ($DP_{calculated}$) until the difference between the last $Re_{est}$ and the current $Re_{est}$ is within an acceptable error range. The iterative process is diagrammatically illustrated in FIG. 3. FIG. 5 graphically illustrates an error function versus Reynolds number.

From the above, it will be appreciated that the present invention apparatus and methodology enables the determination of an accurate Reynolds number value for fluid flows having a low Reynolds number, and also for fluid flows having a Reynolds number that varies during operation of the piping system. An advantage of having an accurate Reynolds number is that fluid flow parameters (e.g., velocity, flow rate, viscosity, etc.) can be more accurately determined than would be typically possible using an assumed or static Reynolds number.

While the invention has been described with reference to an exemplary embodiment, it will be understood by those skilled in the art that various changes may be made and equivalents may be substituted for elements thereof without departing from the scope of the invention. For example, the present invention is described in terms of equations that relate certain parameters. In alternative embodiments, the calculated difference in pressure, and/or a friction factor, etc. could be determined from other means such as tabular data. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A method for determining a parameter of fluid flow within a piping system, comprising the steps of:
   determining a measured velocity of the fluid flow within the piping system using a fluid flow meter;
   determining a measured difference in pressure value within the fluid flow using a differential pressure meter;
   selecting an estimated Reynolds number of the fluid flow;
   determining a calculated difference in pressure value using a model which relates the calculated difference in pressure value to the measured velocity and the estimated Reynolds number of the fluid flow;
   determining a degree of inaccuracy of the estimated Reynolds number using the measured difference in pressure and the calculated difference in pressure;
   iteratively adjusting the estimated Reynolds number, determining the calculated difference in pressure, and determining the degree of inaccuracy using the adjusted Reynolds number, until the degree of inaccuracy is within an acceptable range; and
   determining, using a processor, the parameter of fluid flow using the adjusted estimated Reynolds number.

2. The method of claim 1, wherein the step of determining the measured velocity is performed using a fluid flow meter having ultrasonic sensors.

3. The method of claim 2, wherein the parameter is the velocity of the fluid flow.

4. The method of claim 3, wherein the step of determining a degree of inaccuracy of the estimated Reynolds number includes using an error function that includes the measured difference in pressure and the calculated difference in pressure.

5. The method of claim 1, wherein the step of determining the measured difference in pressure value within the fluid flow is performed using a first pressure transducer located at a first axial position on the piping system, and a second pressure transducer located at a second axial position on the piping system, which first and second axially positions are axially separated from one another.

6. The method of claim 5, wherein the fluid flow meter is disposed on the piping system between the first and second axial positions.

7. An apparatus for determining a parameter of fluid flow within a piping system, comprising:
   a fluid flow meter operable to determine the velocity of the fluid flow within the piping system;
   a differential pressure meter operable to determine a measured difference in pressure within the fluid flow within the piping system;

a processor adapted to receive input including an estimated Reynolds number of the fluid flow, and to determine a calculated difference in pressure value using a model which relates the calculated difference in pressure value to a measured fluid flow velocity and the estimated Reynolds number of the fluid flow, and to determine a degree of inaccuracy of the estimated Reynolds number using the measured difference in pressure and the calculated difference in pressure, and to iteratively adjust the estimated Reynolds number, determine the calculated difference in pressure, and determine the degree of inaccuracy until the degree of inaccuracy is within an acceptable range, and to determine the parameter of the fluid flow within the piping system using the adjusted Reynolds number.

8. The apparatus of claim 7, wherein the fluid flow meter is operable to measure fluid flow velocity using ultrasonic sensors.

9. The apparatus of claim 8, wherein the parameter is the velocity of the fluid flow.

10. The apparatus of claim 9, wherein the processor is adapted to determine the degree of inaccuracy of the estimated Reynolds number using an error function that includes the measured difference in pressure and the calculated difference in pressure.

11. The apparatus of claim 7, wherein the differential pressure meter includes a first pressure transducer locatable at a first axial position on the piping system, and a second pressure transducer locatable at a second axial position on the piping system, which first and second axially positions are axially separated from one another.

12. The apparatus of claim 11, wherein the fluid flow meter is sized to be disposed on the piping system between the first and second axial positions.

* * * * *